(12) United States Patent
Smith (10) Patent No.: US 8,348,968 B2
(45) Date of Patent: Jan. 8, 2013

(54) OBTURATOR TIPS

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 112 days.

(21) Appl. No.: 12/526,059

(22) PCT Filed: Feb. 20, 2008

(86) PCT No.: PCT/US2008/002267
§ 371 (c)(1),
(2), (4) Date: Aug. 6, 2009

(87) PCT Pub. No.: WO2008/103400
PCT Pub. Date: Aug. 28, 2008

(65) Prior Publication Data
US 2010/0318112 A1    Dec. 16, 2010

Related U.S. Application Data (60) Provisional application No. 60/902,676, filed on Feb. 21, 2007.

(51) Int. Cl.
*A61B 17/34* (2006.01)
(52) U.S. Cl. ..................................... 606/185
(58) Field of Classification Search ............... 606/185, 606/167, 170, 184, 171, 80, 183; 604/264, 604/164.01, 164.08, 164.12, 170.01, 164.11, 604/256, 104, 167.01, 167.02; 600/564, 600/567; 408/211, 223, 224, 228; 30/48, 30/346.57, 353; 83/660, 667–669
See application file for complete search history.

(56) References Cited

U.S. PATENT DOCUMENTS

| | | | |
|---|---|---|---|
| 5,562,677 A | | 10/1996 | Hildwein et al. |
| 5,609,604 A | * | 3/1997 | Schwemberger et al. ..... 606/185 |
| 5,645,076 A | | 7/1997 | Yoon |
| 5,674,184 A | * | 10/1997 | Hassler, Jr. .................... 600/176 |
| 5,690,663 A | | 11/1997 | Stephens |
| 5,916,232 A | | 6/1999 | Hart |
| 6,547,802 B1 | * | 4/2003 | Nallakrishnan et al. ....... 606/166 |
| 6,960,164 B2 | * | 11/2005 | O'Heeron ...................... 600/114 |
| 2005/0107816 A1 | * | 5/2005 | Pingleton et al. ............. 606/185 |
| 2005/0203559 A1 | | 9/2005 | O'Heeron |
| 2006/0224174 A1 | | 10/2006 | Smith et al. |
| 2007/0005087 A1 | | 1/2007 | Smith et al. |

OTHER PUBLICATIONS

International Search Report for PCT/US2008/002267—date of mailing is Jul. 25, 2008 (1 page).
European Search Report from EP Application No. EP 10 25 2127 mailed Apr. 17, 2012.

* cited by examiner

*Primary Examiner* — Victor Nguyen
*Assistant Examiner* — Jocelin Tanner (57) ABSTRACT

A trocar assembly for use in minimally invasive surgical procedures includes a cannula subassembly and an obturator subassembly. The obturator assembly includes an obturator shaft member defining a longitudinal axis and an obturator tip configured to be removable from the obturator shaft member or, alternatively, constructed with the obturator member as a single unit. Various designs of the obturator tip are contemplated.

11 Claims, 14 Drawing Sheets

OBTURATOR TIPS

CROSS REFERENCE TO RELATED APPLICATIONS

This application is a National Stage Application of PCT/US2008/002267 filed Feb. 20, 2008 under 35 USC §371(a), which claims the benefit of and priority to U.S. Provisional Patent Application Ser. No. 60/902,676 filed Feb. 21, 2007, the entire disclosure of which is incorporated by reference herein.

BACKGROUND

1. Technical Field

The present invention relates to an apparatus for penetration of body tissue. More particularly, the present invention relates to an obturator assembly for use with a trocar assembly and having a variety of tapered tip configurations.

2. Background of Related Art

In endoscopic surgical procedures, surgery is typically performed through narrow endoscopic tubes (cannulas) inserted through a small entrance wound in the skin. In laparoscopic procedures, surgery is performed in the interior of the abdomen. Generally, after the surgical region is insufflated, a trocar is used to puncture the body cavity and a cannula which receives the obturator remains in place for use during the laparoscopic procedure. Typically, a trocar includes an obturator having a sharp tip for penetrating the body cavity. Benefits with use of trocars in laparoscopic surgery include less trauma to the patient and reduced recovery time.

SUMMARY

Accordingly, the present disclosure relates to further improvements in accessing/penetrating body tissue during a surgical procedure, preferably, a laparoscopic procedure. The present disclosure is directed to a trocar assembly for use in minimally invasive surgical procedures including a cannula subassembly and an obturator subassembly.

In one embodiment, an obturator for use in penetrating tissue includes an elongate obturator member defining a longitudinal obturator axis and an obturator tip. The obturator tip defines a base member connectable to the obturator member and a tapered tip member extending from the base member to a penetrating end. The tip member has an elliptical cross-sectional configuration and is devoid of peripheral cutting edges. The penetrating end may be defined at a point generally coinciding with the longitudinal axis of the elongate obturator member. The tip member may include a proximal tip portion and a distal tip portion. The proximal tip portion has an elliptical cross-sectional dimension defining a major axis and a minor axis, whereby along a length of the proximal tip portion the major axis is substantially constant and the minor axis increases from distal to proximal. The distal tip portion has an elliptical cross-sectional dimension defining a major axis and a minor axis whereby along a length of the distal tip portion the major axis and the minor axis increase from distal to proximal. The tip member defines an outer surface having a generally parabolic contour.

In another embodiment, a surgical obturator for use in penetrating tissue includes an elongate obturator member defining a longitudinal obturator axis and an obturator tip. The obturator defines a base member connectable to the obturator member and a tapered tip member extending from the base member to a penetrating end. The tip member has at least two surfaces intersecting along a line of intersection which traverses the longitudinal axis. The penetrating end generally coincides with the longitudinal axis of the base portion. At least two surfaces intersect along the line of intersection which is generally transverse to the longitudinal axis. A first surface of the at least two surfaces extends contiguously from the penetrating end and is in general parallel relation to the longitudinal axis. A second surface of the at least two surfaces may extend contiguously from the first surface and is in oblique relation with the longitudinal axis. A third surface of the at least two surfaces may extend contiguously from the second surface and is in oblique relation with the longitudinal axis. The first, second and third surfaces may be substantially planar. First and second pairs of each of the first, second and third surfaces may be provided. Each of the surfaces of the respective pairs are arranged in diametrical opposed relation.

In another embodiment, a surgical obturator for use in penetrating tissue includes an elongate obturator member defining a longitudinal obturator axis and an obturator tip. The obturator tip includes a base member connectable to the obturator member and a tip member extending from the base member to a penetrating end. The tip member defines a complex curve configuration to extend in a non-linear manner along the longitudinal axis from the base member to a penetrating end which generally coincides with the longitudinal axis of the base portion. The tip member may define a general parabolic configuration along the longitudinal axis. Alternatively, the tip member defines an outer wall having a first pair of opposed generally convex surfaces and a second pair of generally opposed concave surfaces.

In another embodiment, a surgical obturator for use in penetrating tissue includes an elongate obturator member defining a longitudinal obturator axis and an obturator tip. The obturator tip defines a base member connectable to the obturator member and a tip member extending from the base member to a penetrating end. The tip member includes, from distal to proximal, a first pair of diametrically opposed substantially planar surfaces extending from the penetrating end toward the base member and being in general parallel relation with the longitudinal axis, a second pair of diametrically opposed surfaces in general alignment with the longitudinal axis, third and fourth pairs of diametrically opposed surfaces disposed radial outwardly on respective sides of the second pair of opposed surfaces and fifth and sixth pairs of diametrically opposed surfaces disposed radial outwardly on respective sides of the third and fourth pairs of opposed surfaces. The surfaces of at least the second, third, and fourth pairs of surfaces may be generally concave.

In another embodiment, a surgical obturator for use in penetrating tissue includes an elongate obturator member defining a longitudinal obturator axis and an obturator tip. The obturator tip defines a base member connectable to the obturator member and a tip member extending from the base member to a penetrating end. The tip member defines a generally tapered configuration extending along the longitudinal axis from the base member to a penetrating end. The tip member has at least one outer curved surface. The penetrating end is generally displaced from the longitudinal axis of the base member. The at least one outer curved surfaces may be generally concave. In the alternative, the tip member includes at least three intersecting surfaces, namely, a first centrally positioned surface in general alignment with the longitudinal axis, and second and third surfaces radially outward of the first surface. The first surface may be substantially planar or substantially arcuate.

In another embodiment, a surgical obturator for use in penetrating tissue includes an elongate obturator member defining a longitudinal obturator axis and an obturator tip defining a base member connectable to the obturator member and a tip member extending from the base member to a penetrating end. The tip member defines a generally tapered configuration extending along the longitudinal axis from the base member to a penetrating end. The tip member includes first and second diametrically opposed wings extending from an outer wall of the tip member. The wings define a cross-sectional dimension which increases from distal to proximal. The first and second diametrically opposed wings may define peripheral cutting edges.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein: said

FIG. 12AA is a cross sectional view of the penetrating end of FIG. 12;

DESCRIPTION OF EMBODIMENTS

Figures 1, 2:
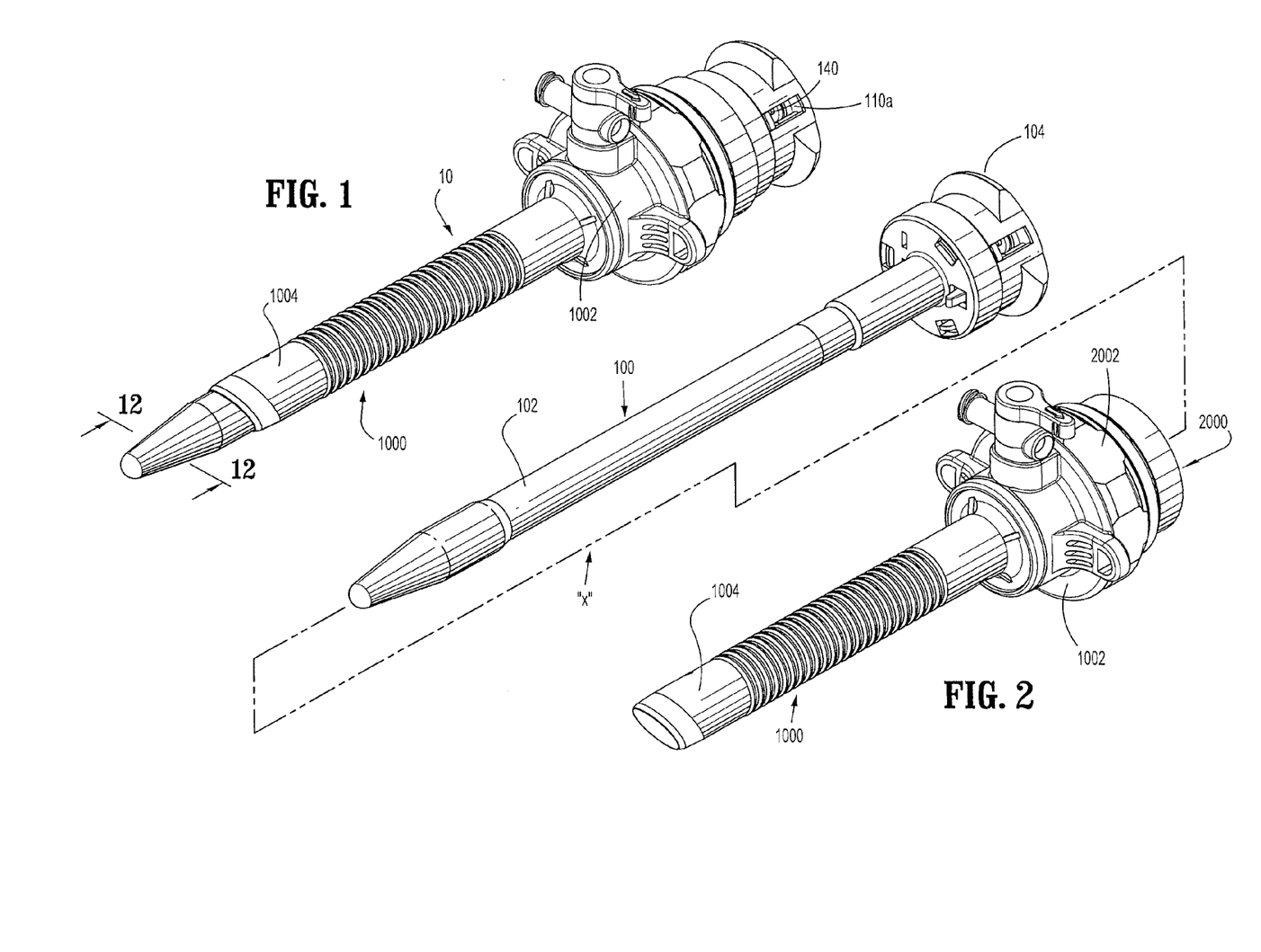
FIG. 1 is a perspective view of a surgical trocar assembly including a cannula and an obturator in accordance with the principles of the present disclosure.
FIG. 2 is a perspective view with parts separated of the surgical trocar assembly including a cannula and an obturator of FIG. 1.

Referring now in detail to the drawing Figures, in which, like reference numerals identify similar or identical elements, there is illustrated, in FIGS. 1 and 2, a trocar assembly constructed in accordance with a preferred embodiment of the present disclosure and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Obturator assembly 100 includes obturator housing 102 and elongated obturator member 104 extending distally from the housing 102. Obturator member 104 defines a longitudinal obturator axis "X" and will be discussed in greater detail hereinbelow.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part or in whole and may be fabricated from biocompatible metal or polymeric material. Cannula assembly 1000 may include an internal seal such as a duck-bill valve or other zero closure valves adapted to close in the absence of a surgical instrument to prevent passage of insufflation gases through the cannula assembly 1000.

Trocar assembly 10 may also include a seal assembly 2000 which is preferably releasably mounted to cannula housing 1002. Means for releasably connecting seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal which is adapted to form a fluid tight seal about an instrument inserted through the seal assembly 2000. One suitable seal may be the fabric seal disclosed in commonly assigned U.S. Pat. No. 6,702,787, which issued Mar. 9, 2004, the entire contents of which are incorporated herein by reference. The seal disclosed in the '630 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Figure 3:
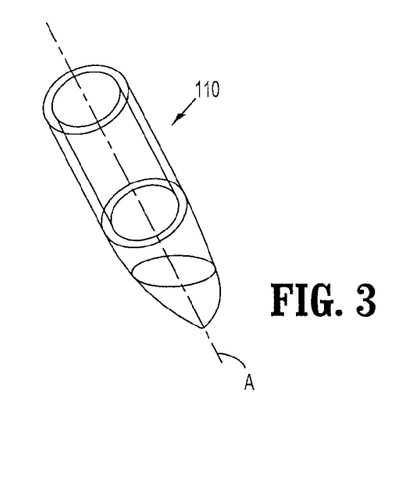
FIG. 3 is a perspective view of the penetrating end of the surgical obturator of FIG. 2.
Figure 3A:
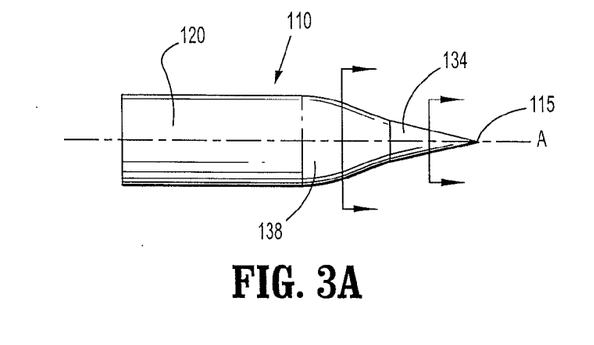
FIG. 3A is a first side plan view of the penetrating end of the surgical obturator of FIG. 3.
Figure 3B:
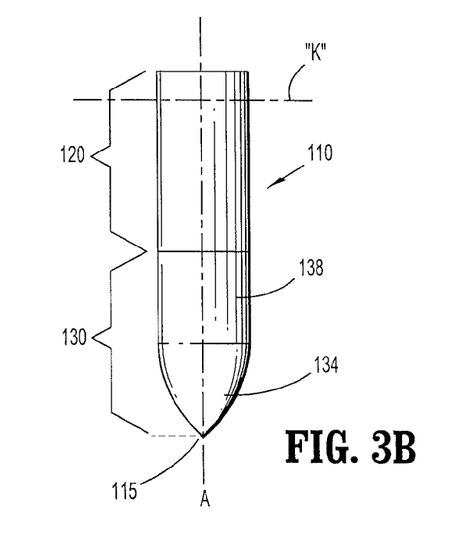
FIG. 3B is a second side plan view of the penetrating end of the surgical obturator of FIG. 3.
Figure 3C:
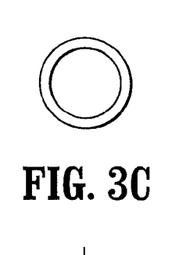
FIG. 3C is an axial view of the proximal end of the penetrating end of the surgical obturator of FIG. 3.
Figure 3D:
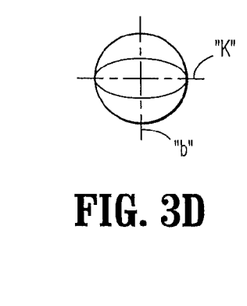
FIG. 3D is an axial view of the distal end of the penetrating end of the surgical obturator of FIG. 3.

Referring now to FIGS. 3-3D, in conjunction with FIG. 2, there is illustrated a surgical obturator tip in accordance with one embodiment of the present disclosure. Obturator tip 110 includes two components, namely, a base member 120 defined along longitudinal axis "A" and a tip member 130. Tip member 130 of obturator tip 110 generally tapers inwardly relative to longitudinal axis "X" towards a penetrating end 115 and is defined by a generally elliptical cross-sectional configuration. Tip member 130 defines a leading tip section 134 adjacent penetrating end 115 and a trailing tip section 138 adjacent base member 120. Leading tip section 134 defines an elliptical cross-sectional dimension having a major axis "k" and a minor axis "b" (FIG. 3D). As best depicted in FIG. 3A, the dimension measured along the "b" axis of leading tip section 134 gradually increases from penetrating end 115 to the area of intersection of leading and trailing tip sections 134, 138, preferably in a linear manner. The dimension measured along the "k" axis and corresponding to the major axis of the ellipse, increases from penetrating end 115 to the area of intersection of leading and trailing tip sections 134, 138. As best depicted in FIG. 3B, this taper is preferably asymptotic or parabolic in character. Trailing tip section 138 has a dimension measured along the "b" axis which gradually increases from the area of intersection of leading and trailing tip sections 134, 138 to base member 120. The taper may be linear or parabolic. The dimension measured along the "k" axis is constant and is equivalent to the major dimension or diameter of base member 120 as depicted in FIG. 3B. Penetrating end 115 is defined at a point generally coinciding with longitudinal axis "X", and may have a sharpened edge or may be generally blunt if desired. As to be appreciated, obturator tip 110 may be configured to be removable from the obturator member 1004 or constructed with the obturator member 1004 as a single unit. If unable, obturator tip 110 may be connected to obturator member 1004 by conventional means including frictional or interference fits, bayonet couplings, screw threads, etc.

Figure 4:
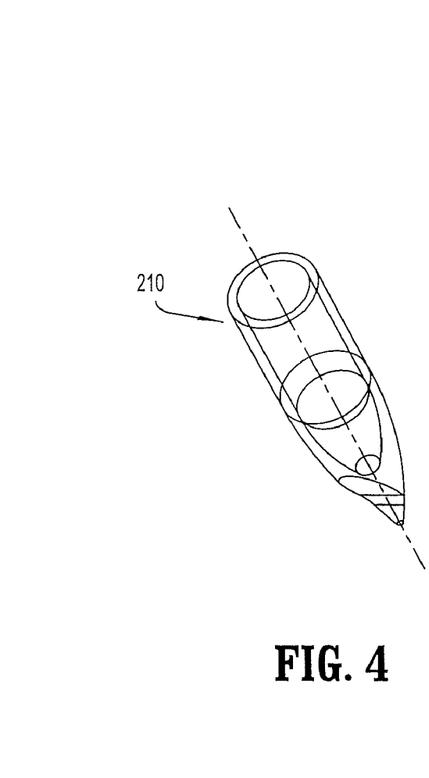
FIG. 4 is a perspective view of an alternate embodiment of the penetrating end of the surgical obturator.
Figure 4A:
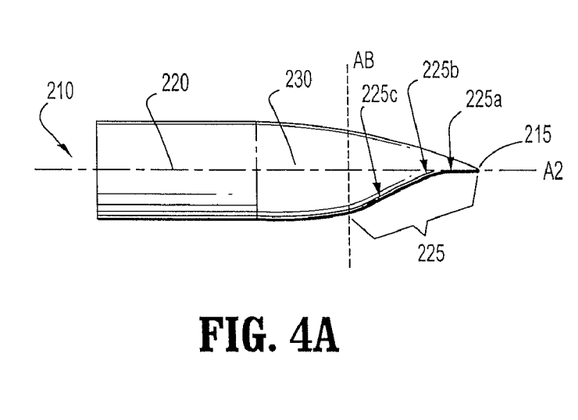
FIG. 4A is a first side plan view of the penetrating end FIG. 4, illustrating the angles of the planar surfaces defining the chamfered portion of the tip member.
Figure 4B:
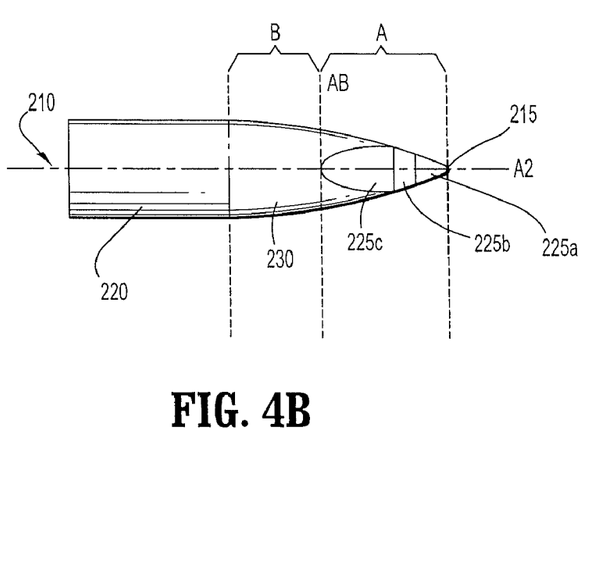
FIG. 4B is a second side plan view of the penetrating end of FIG. 4, illustrating the relationship between the planar surfaces of the chamfered portion.
Figure 4C:
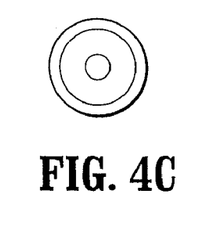
FIG. 4C is an axial view of the penetrating end of FIG. 4.

Referring now to FIGS. 4-4C, in conjunction with FIG. 2, there is illustrated a surgical obturator tip in accordance with an alternative embodiment of the present disclosure. In this embodiment, tip member 230 of obturator tip 210 generally tapers inwardly relative to longitudinal axis "X" towards a penetrating end 215 and includes a first tip member section "A" defined between the penetrating end 215 and a longitudinal location "AB" and a second tip member section "B" defined between longitudinal location "AB" and base member 220. Penetrating end 115 is defined at a point generally coinciding with longitudinal axis "X", and may have a sharpened edge or may be generally blunt if desired.

In a first configuration of tip member 230 depicted in FIG. 4, section "B" defines a generally circular cross-sectional configuration from base member 220 to longitudinal location "AB" and section "A" defines a plurality of different cross-sectional shapes formed by a chamfered portion 225. As illustrated in a first profile of tip member 230 depicted in FIG. 4A, chamfered portion 225 extends from penetrating end 215 proximally to longitudinal location "AB." Chamfered portion 225 is defined by a series of intersecting substantially planar surfaces 225a, 225b, and 225c on one arc segment of the chamfered portion 225. Specifically, a first planar surface 225a generally coinciding with longitudinal axis "X" is defined adjacent the penetrating end 215 and extends proximally to intersect a second planar surface 225b proximal to surface 225a defined on an oblique angle with respect to longitudinal axis "X." Surface 225a extends proximally to intersect a third planar surface 225c proximal to surface 225b defined on an oblique angle with respect to longitudinal axis "X". Surface 225c extends proximally to longitudinal location "AB". A second profile (rotated 90°) of tip member 230 depicted in FIG. 4B illustrates in detail the relationship between planar surfaces 225a, 225b, and 225c. As to be appreciated, planar surfaces 225a, 225b, and 225c may vary in angle and/or dimension relative to one another to achieve a desired result, e.g., improvement in penetrating tissue.

Figure 5:
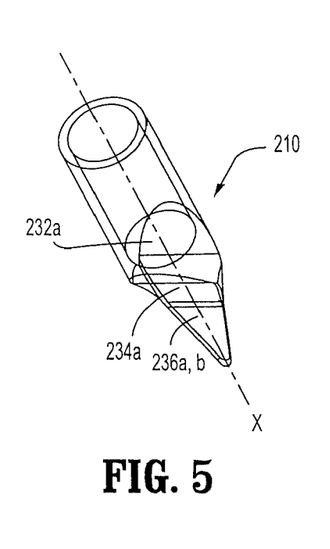
FIG. 5 is a perspective view of an alternate embodiment of the penetrating end of the surgical obturator.
Figure 5A:
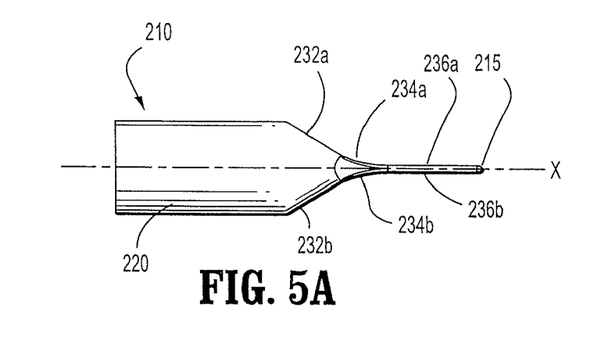
FIG. 5A is a first side plan view of the penetrating end of FIG. 5, illustrating the relationship between the opposed planar surfaces defining the tip member.
Figure 5B:
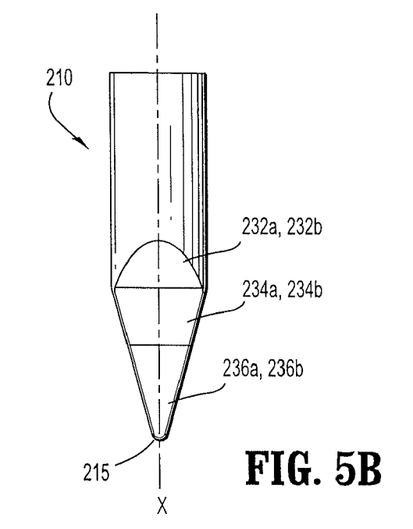
FIG. 5B is a second side plan view of the penetrating end of FIG. 5, illustrating the generally tapered configuration of the tip member.
Figure 5C:
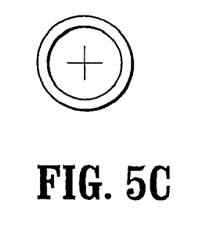
FIG. 5C is an axial view of the proximal end of the penetrating end of FIG. 5.
Figure 5D:
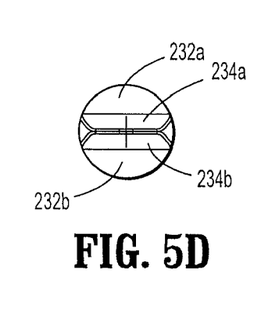
FIG. 5D is an axial view of the distal end of the penetrating end of FIG. 5.

In an alternate embodiment of tip member 230 depicted in FIG. 5-5D, the tip member defines a first pair of opposed planar surfaces 232a, 232b each extending distally from base member 210 at an oblique angle toward longitudinal axis "X" to intersect with a second pair of opposed surfaces 234a, 234b. Surfaces 234a, 234b may be planar or slightly concave in character as shown. With reference now to section "A" of tip member 230, a unique cross-sectional configuration is formed by surfaces 234a, 234b each extending distally from longitudinal location "AB" at an oblique angle toward longitudinal axis "X" to intersect with a third pair of opposed surfaces 236a, 236b. Surfaces 236a, 236b may be substantially planar and extend distally along longitudinal axis "X" in parallel relation to penetrating end 215. This feature presents a relatively narrow profile which facilitates entry and initial passage through tissue. As depicted in FIG. 5B, penetrating end 215 is defined by a slightly arcuate configuration. A pointed configuration of penetrating end 215 is also contemplated.

Figures 6, 6A, 6B, 6C:
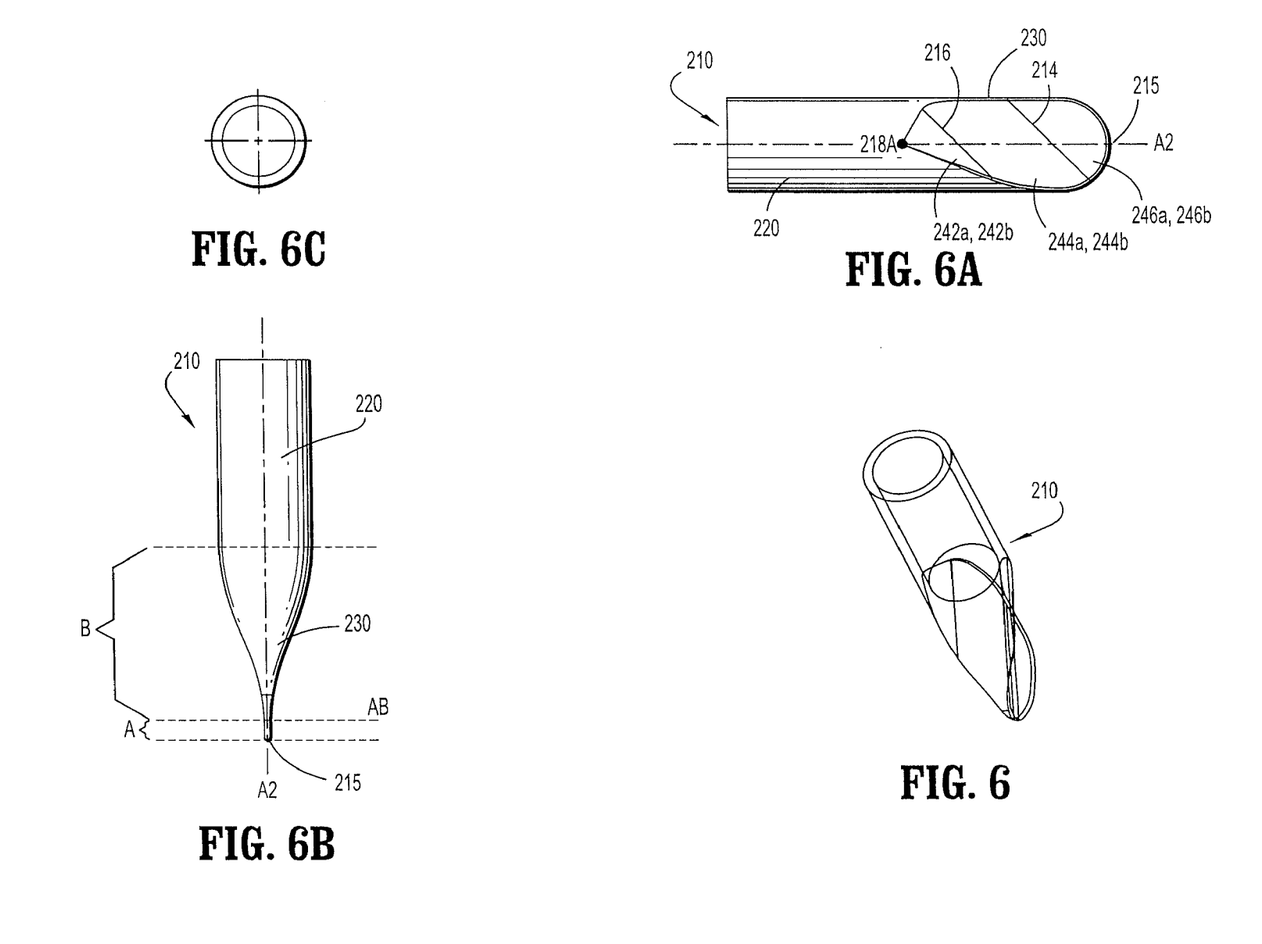
FIG. 6 is a perspective view of an alternate embodiment of the penetrating end of the surgical obturator.
FIG. 6A is a first side plan view of the penetrating end of FIG. 6, illustrating the relationship between the opposed planar surfaces defining the tip member.
FIG. 6B is a second side plan view of the penetrating end of FIG. 6, illustrating the generally tapered configuration of the tip member.
FIG. 6C is an axial view of the penetrating end of the surgical obturator of FIG. 6.

In another embodiment depicted in FIGS. 6A-6C, tip member includes a first pair of opposed planar surfaces 242a, 242b, generally triangular in shape, originating at a first intersecting point 218A defined along longitudinal axis "X", each extending distally and at an oblique angle toward longitudinal axis "X" to intersect with a corresponding second pair of opposed planar surfaces 244a, 244b along lines of intersection 216. Surfaces 244a, 244b are generally quadrilateral in shape and each extend distally from lines of intersection 216 at an oblique angle toward longitudinal axis "X" to intersect with a third pair of opposed planar surfaces 246a, 246b along lines of intersection 214. Surfaces 246a, 246b are generally parallel to each other and extend distally penetrating end 215.

Figure 7:
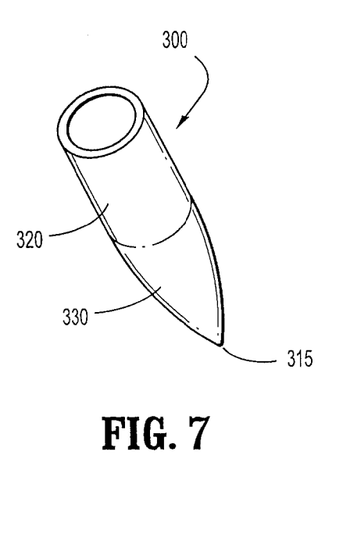
FIG. 7 is a perspective view of an alternate embodiment of the penetrating end of the surgical obturator.
Figure 7A:
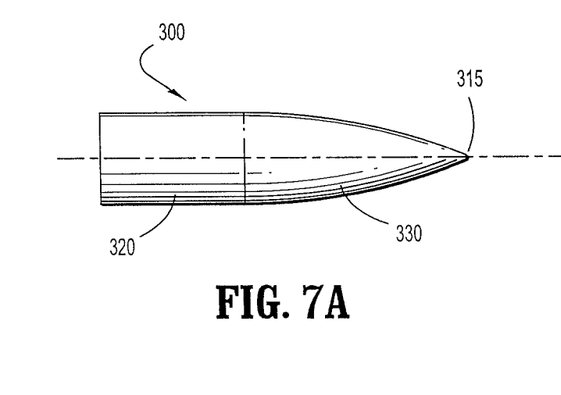
FIG. 7A is a first side plan view of the penetrating end of FIG. 7, illustrating the complex curve configuration defined by the tip member.
Figure 7B:
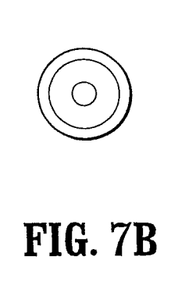
FIG. 7B is an axial view of the penetrating end of FIG. 7.

Referring now to FIGS. 7-7B, there is illustrated another embodiment of a surgical obturator in accordance with the present disclosure. Obturator 300 includes two components, namely, base member 320 defined along longitudinal axis "X" and a tip member 330. Tip member 330 defines a complex curve configuration and extends in a non-linear manner along longitudinal axis "X" from base member 320 to a penetrating end 315. Penetrating end 315 is defined at a point generally coinciding with longitudinal axis "X."

In a first configuration of tip member 330 depicted in FIG. 7, tip member 330 is defined along longitudinal axis "X" and is generally parabolic in shape. Penetrating end 315 is shown to have a pointed configuration; however, a slightly arcuate configuration is also contemplated.

Figure 8:
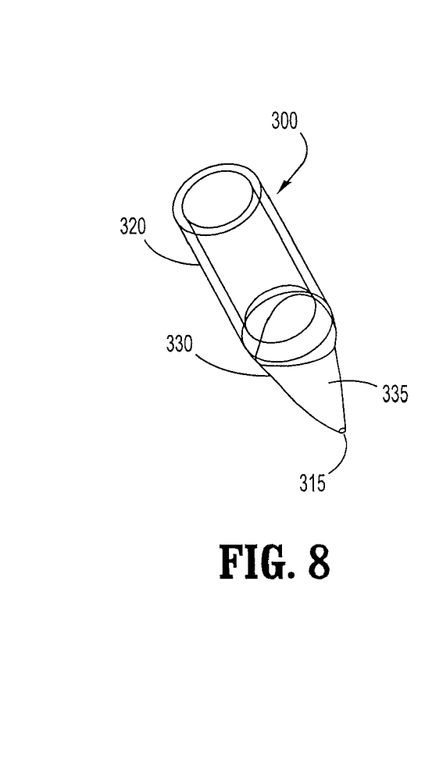
FIG. 8 is a perspective view of an alternate embodiment of the penetrating end of the surgical obturator.
Figure 8A:
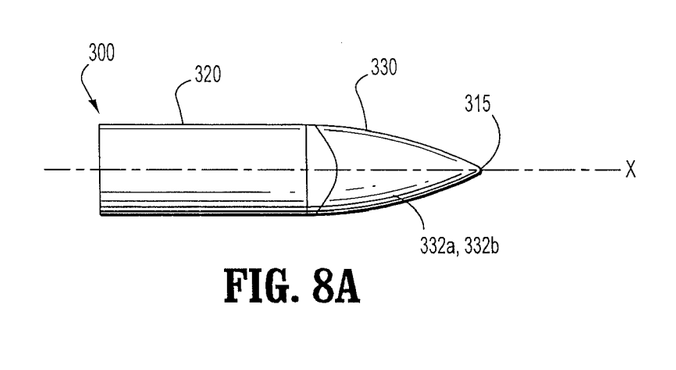
FIG. 8A is a first side plan view of the penetrating end of FIG. 8, illustrating the opposed generally convex surfaces defining the outer wall of the tip member.
Figure 8B:
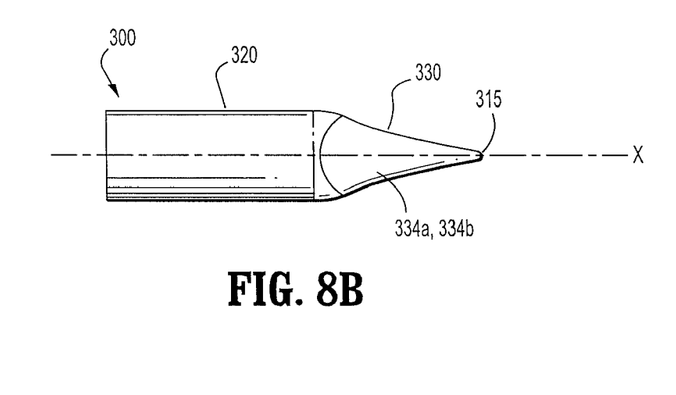
FIG. 8B is a second side plan view of FIG. 8, illustrating the opposed generally concave surfaces defining the outer wall of the tip member.
Figure 8C:
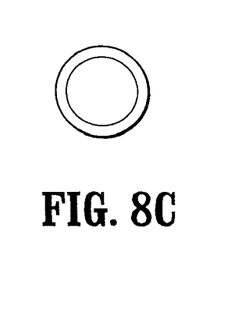
Figure 9:
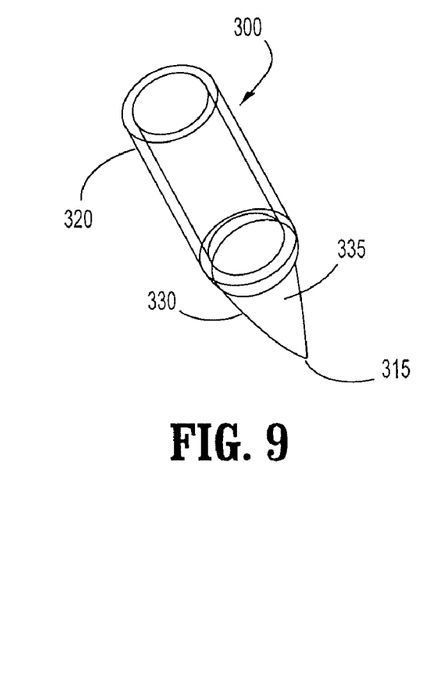
FIG. 9 is a perspective view of an alternate embodiment of the penetrating end of the surgical obturator in accordance with the embodiment of FIG. 8, illustrating the more pointed penetrating end configuration.
Figure 9A:
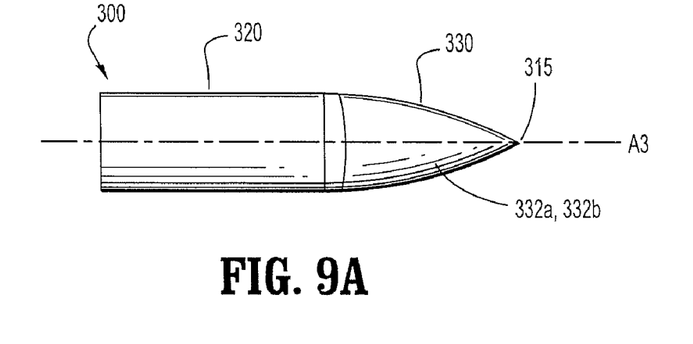
FIG. 9A is a first side plan view of the penetrating end of FIG. 9, illustrating the opposed generally convex surfaces defining the outer wall of the tip member.
Figure 9B:
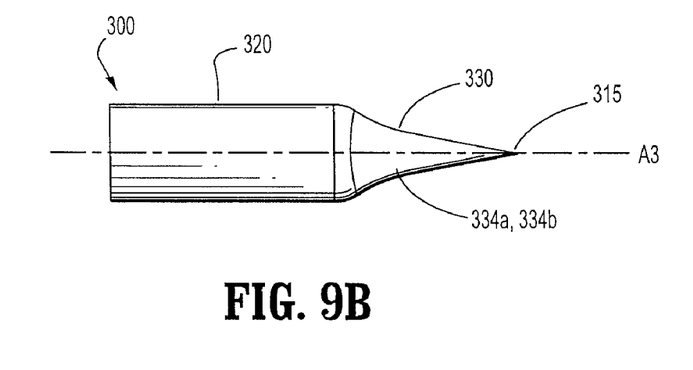
FIG. 9B is a second side plan view of FIG. 9, illustrating the opposed generally concave surfaces defining the outer wall of the tip member.
Figure 9C:
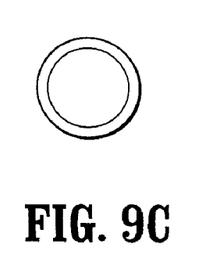
FIG. 9C is an axial view of the penetrating end of FIG. 9.

In an alternate embodiment depicted in FIGS. 8-8C, tip member 330 is defined by an outer wall 335 extending from base portion 320 to penetrating end 315. Outer wall 335 defines a first pair of opposed generally convex surfaces 332a, 332b and a second pair of opposed generally concave surfaces 334a, 334b when rotating the tip member 330 90° (see FIGS. 8A and 8D). Convex surfaces 332a, 332b and concave surfaces 334a, 334b converge at a point generally coinciding with longitudinal axis "X" to define a blunt tip configuration of penetrating end 315. Surfaces 332a, 332b and surfaces 334a, 334b are configured in an alternating arrangement to provide outer wall 335 with an enhanced ability to penetrate or pass through tissue layers. Tip member 330 as depicted in FIG. 8, by its blunt tip configuration, minimizes the potential of undesired or unintended piercing of tissue. FIGS. 9, 9A, and 9B illustrate a tip member similar to the embodiment of FIG. 8, but, including a pointed tip configuration 315 to assist in piercing tissue.

Figure 10:
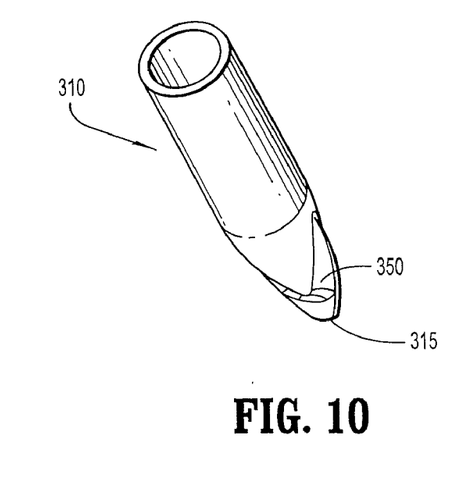
FIG. 10 is a perspective view of an alternate embodiment of the penetrating end of the surgical obturator.
Figure 10A:
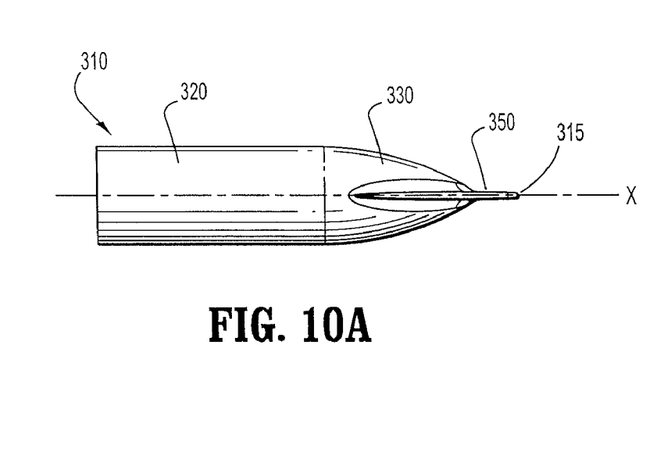
FIG. 10A is a side plan view of the penetrating end of FIG. 10, illustrating the opposed substantially planar surfaces intersecting at the penetrating tip.
Figure 10B:
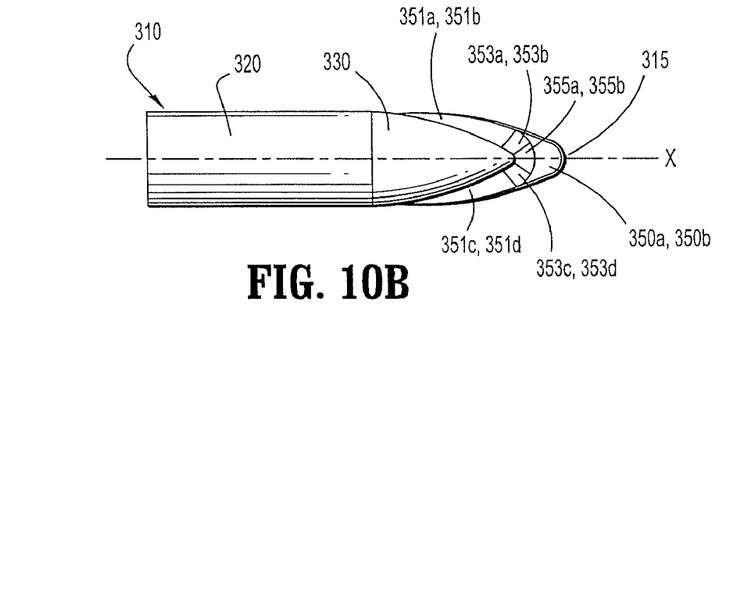
FIG. 10B is a second side plan view of the penetrating end of FIG. 10, illustrating the relationship between the opposed substantially planar surfaces defining the tip member.
Figure 10C:
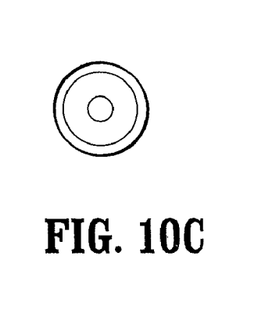
FIG. 10C is an axial view of the penetrating end of the surgical obturator of FIG. 10.

FIGS. 10-10C illustrate another embodiment of the tip member 330. The tip member 330 includes a first pair of opposed planar surfaces 350a, 350b extending from penetrating end 315 and in parallel relation to the longitudinal axis "x". Proximal of planar surfaces 350a, 350b are a series of intersecting surfaces symmetrically arranged about the longitudinal axis "x". These surfaces include centrally disposed surface 355, a pair of surfaces 353 on each side of the centrally disposed surface 355, a second pair of surfaces 351 on each side of the surfaces 353. Surfaces 351 extend in a proximal location towards base 320. Each of surfaces 355,353,351 may be arcuate, e.g., generally concave, or planar. Penetrating tip 315 is generally aligned with the longitudinal axis "x".

Figure 11:
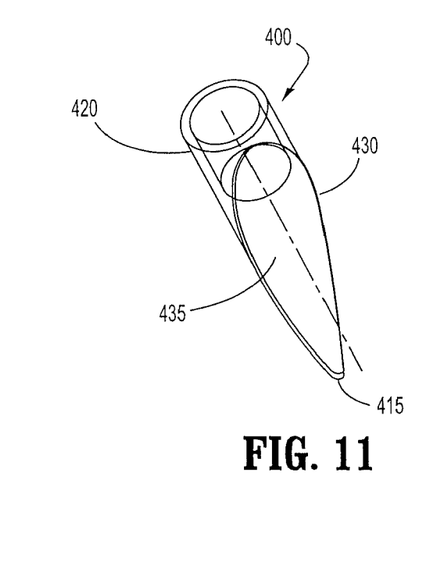
FIG. 11 is a perspective view of an alternate embodiment of the penetrating end of the surgical obturator.

Referring now to FIG. 11, there is illustrated yet another embodiment of a surgical obturator in accordance with the present disclosure. Obturator 400 includes two components, namely, a base member 420 defined along a longitudinal axis "X" and an atraumatic tip member 430. Tip member 430 includes at least one outer curved surface and defines a generally tapered configuration extending along longitudinal axis "X" from base member 420 to a penetrating end 415. Penetrating end 415 is defined at a point generally displaced from longitudinal axis "X."

Figure 11A:
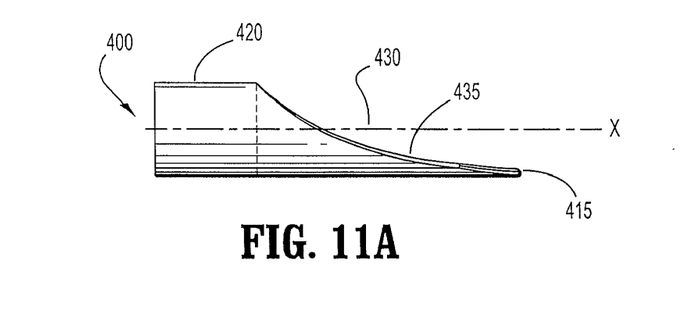
FIG. 11A is a first side plan view of the penetrating end of FIG. 11, illustrating both the angle of the outer curved surface with respect to the longitudinal axis and the generally displaced position of the penetrating end relative to the longitudinal axis.
Figures 11B, 11C:
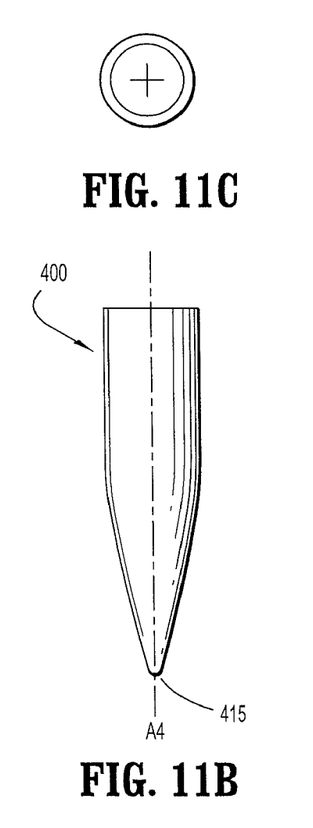
FIG. 11B is a second side plan view of the penetrating end of FIG. 11, illustrating the generally tapered configuration of the tip member.
FIG. 11C is an axial view of the penetrating end of FIG. 11.

Tip member 430 includes outer curved surface 435. Surface 435 tapers away from the base member 420 and is beveled downward, as shown in FIG. 11A, from the distal end of base portion 420 to penetrating end 415. Surface 435 is generally arcuate or generally concave in configuration. Penetrating end 415 may be sharp or blunt and is displaced from the longitudinal axis "X".

Figures 12, 12A, 12B, 12C, 12D:
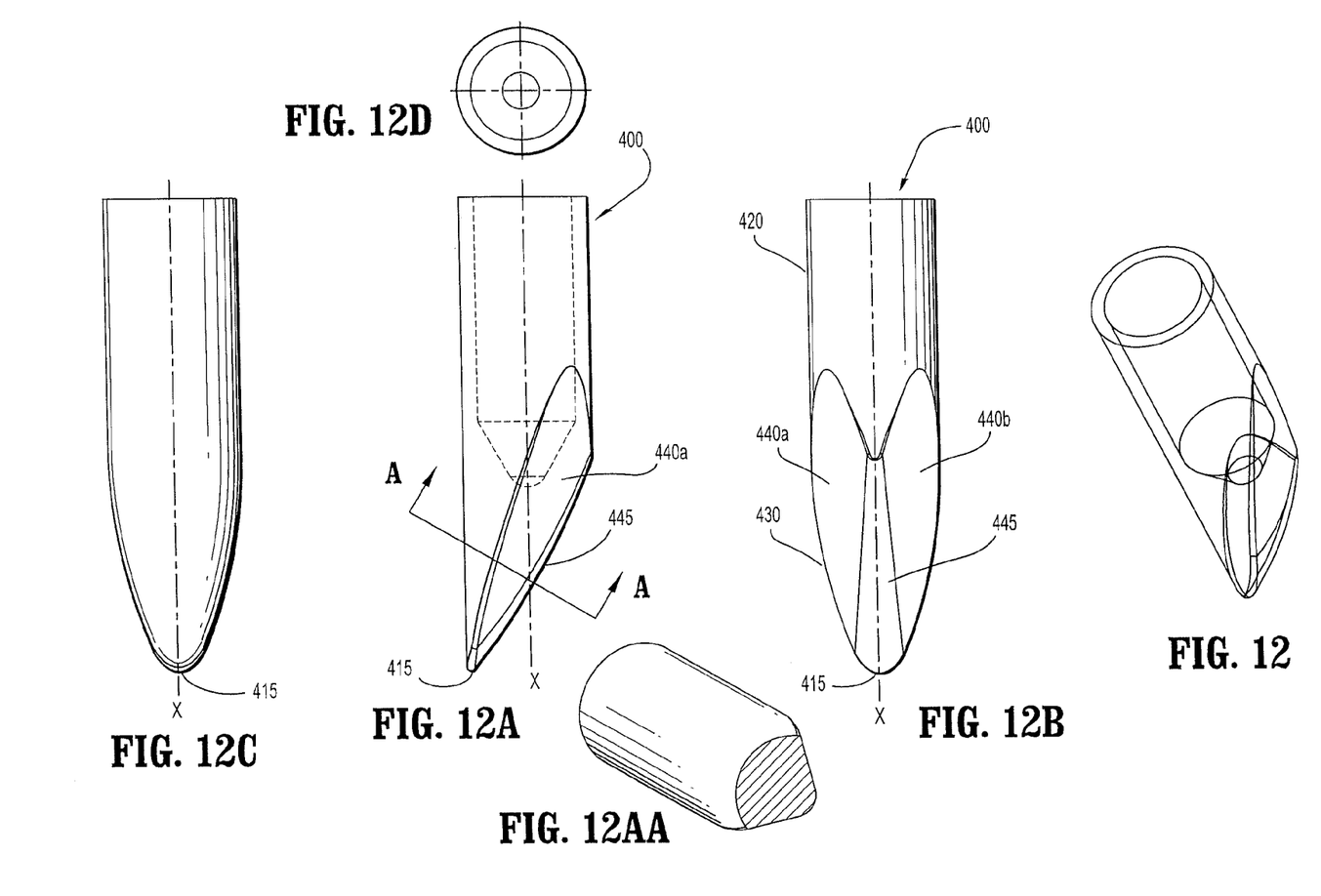
FIG. 12 is a perspective view of an alternate embodiment of the penetrating end of the surgical obturator in accordance with the embodiment of FIG. 11.
FIG. 12A is a side plan view of the penetrating end of FIG. 12, illustrating the angle of both the opposed outer curved surfaces and the angled surface with respect to the longitudinal axis.
FIG. 12B is a first plan view of the penetrating end of FIG. 12, illustrating the relationship between the opposed outer curved surfaces and the angled surface therebetween.
FIG. 12C is a second plan view of the penetrating end of FIG. 12, illustrating the generally tapered configuration of the tip member.
FIG. 12D is an axial view of the penetrating end of FIG. 12.

In another embodiment depicted in FIG. 12, tip member 430 includes a pair of opposed outer curved surfaces 440a, 440b which intersect an angled surface 445 defined therebetween. As can be seen in FIG. 12C, angled surface 445 intersects surfaces 440a, 440b at penetrating end 415 and extends proximally to intersect surfaces 440a, 440b slightly proximal to base member 420. Surface 445 is preferably generally arcuate in configuration and may be generally concave or generally convex. Surfaces 440a, 440b may be planar or substantially arcuate (e.g., generally concave or generally convex) in configuration. FIG. 12B, penetrating end 415 defines a generally arcuate or blunt configuration. Alternatively, it is envisioned that penetrating end 415 may be more pointed, to facilitate tissue piercing if desired.

Figure 13:
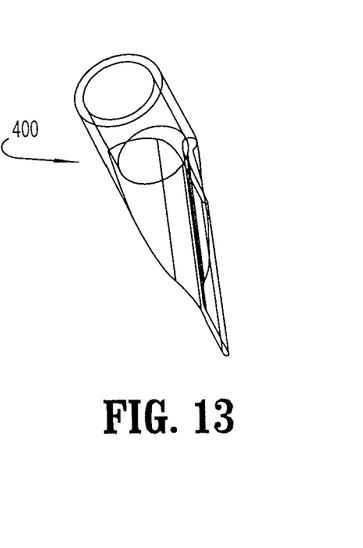
FIG. 13 is a perspective view of an alternate embodiment of the penetrating end of the surgical obturator.
Figure 13A:
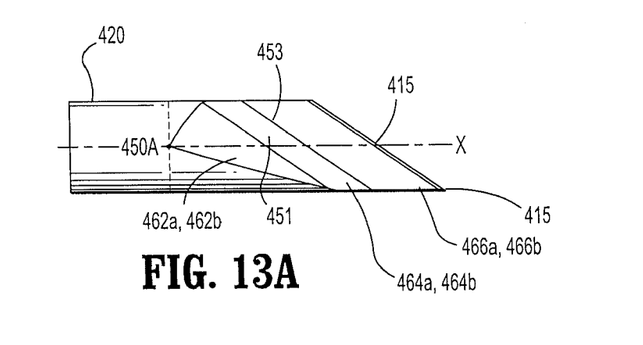
FIG. 13A is a first side plan view of the penetrating end of FIG. 13, illustrating the relationship between the opposed generally planar surfaces.
Figure 13B:
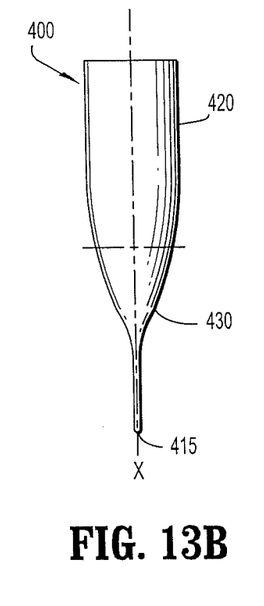
FIG. 13B is a second side plan view of the penetrating end of FIG. 13, illustrating the generally tapered configuration of the tip member.
Figure 13C:
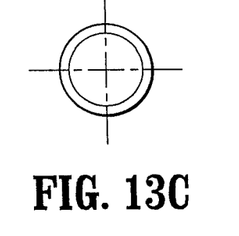
FIG. 13C is an axial view of the penetrating end of FIG. 13.

In another embodiment depicted in FIG. 13, tip member 430 defines a first pair of opposed planar surfaces 462a, 462b which are generally triangular in shape. Specifically, surfaces 462a, 462b originate at a first intersecting point 450A defined at the proximal end of tip member 430 collinear to longitudinal axis "X". Surfaces 462a, 462b each extend distally and at an oblique angle toward longitudinal axis "X" to intersect with a corresponding second pair of opposed planar surfaces 464a, 464b at lines of intersection 451. Surfaces 464a, 464b are generally quadrilateral in shape and each extends distally at an oblique angle toward longitudinal axis "X" to intersect with a third pair of opposed planar surfaces 466a, 466b at a lines of intersection 453. Surfaces 466a, 466b are substantially parallel to each other and the longitudinal axis, and extend distally along longitudinal axis "X" to penetrating edge 415. Penetrating edge 415 may be relatively sharp or substantially blunt.

Figures 14, 14A, 14B, 14C, 14D:
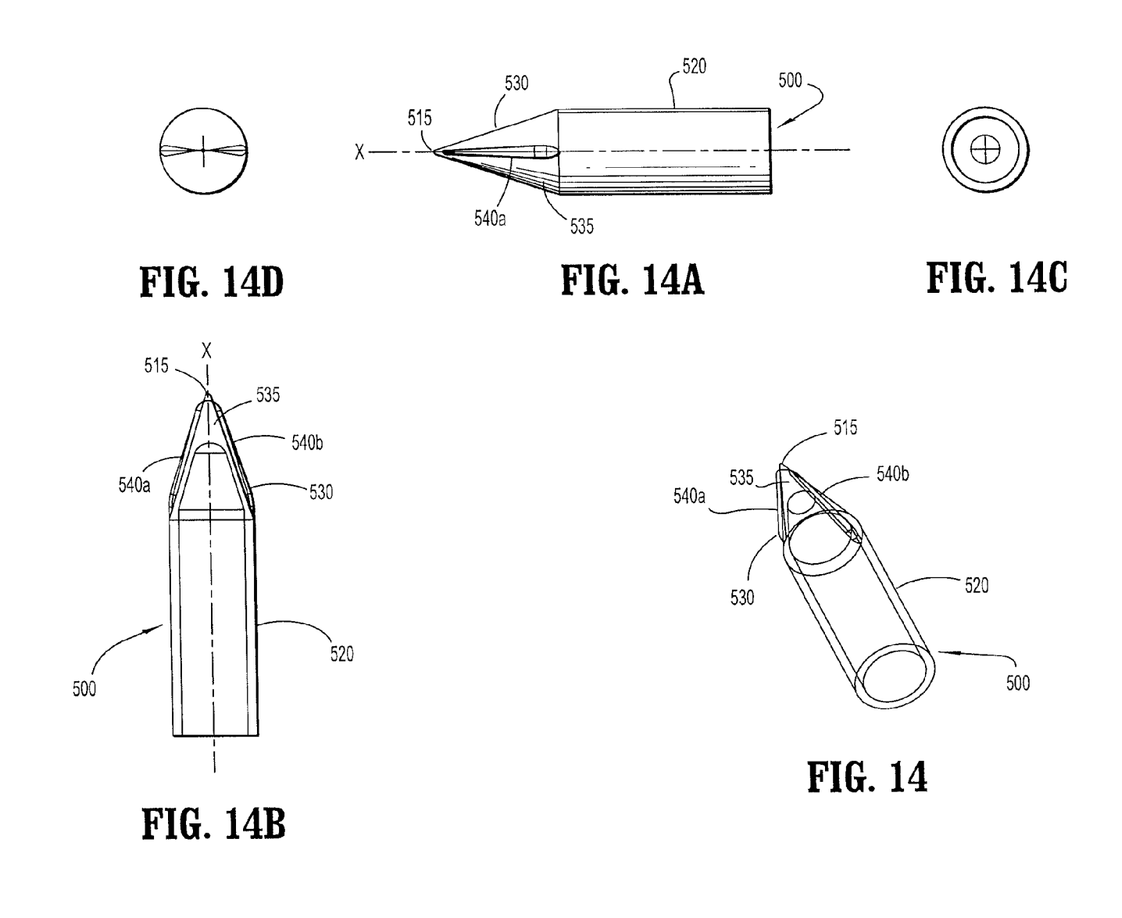
FIG. 14 is a perspective view of an alternative embodiment of the penetrating end of the surgical obturator.
FIG. 14A is a first side plan view of the penetrating end of FIG. 14, illustrating the cross-sectional dimension of the diametrically opposed wing members.
FIG. 14B is a second plan view of the penetrating end of FIG. 14, illustrating the generally tapered configuration of the tip member.
FIG. 14C is an axial view of the distal end of the penetrating end of FIG. 14, illustrating the cross-sectional dimension defined by the wing members.
FIG. 14D is an axial view of the proximal end of the penetrating end of FIG. 14.
Figure 15:
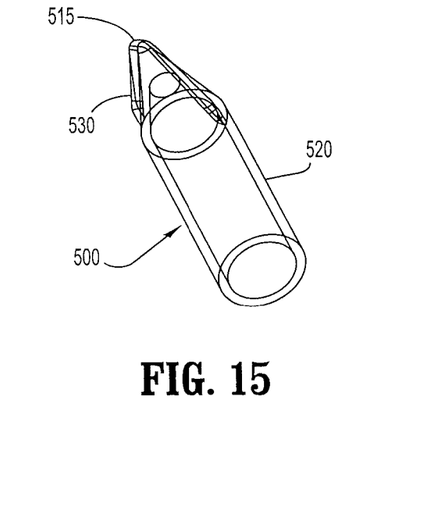
FIG. 15 is a perspective view of an alternate embodiment of the penetrating end of the surgical obturator.
Figure 15A:
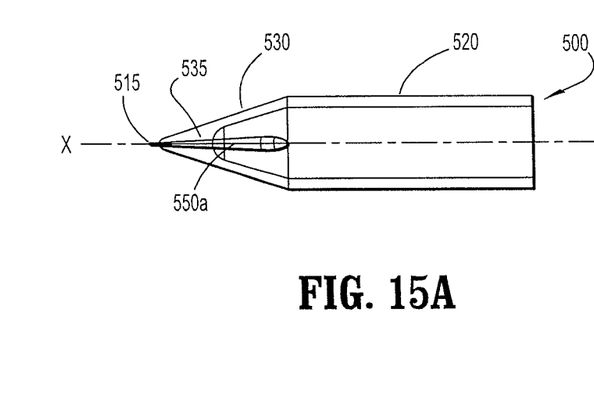
FIG. 15A is a first side plan view of the penetrating end of FIG. 15.
Figure 15B:
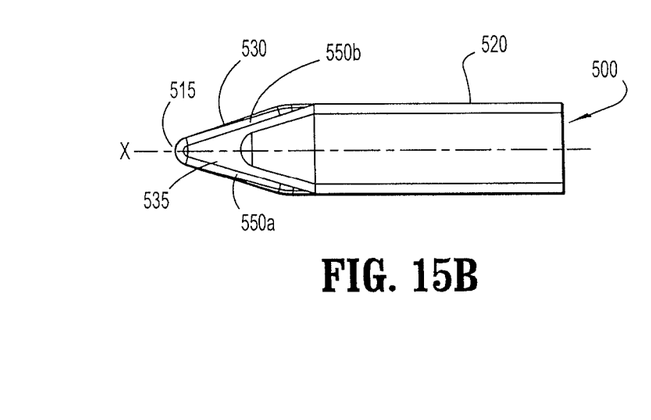
FIG. 15B is a second side plan view of the penetrating end of FIG. 15, illustrating the arcuate configuration of the penetrating end of the tip member.
Figure 15C:
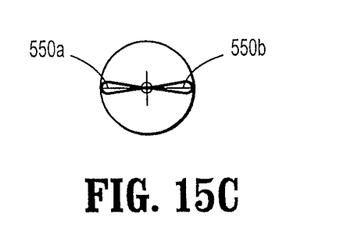
FIG. 15C is an axial view of the distal end of the penetrating end of FIG. 15, illustrating the cross-sectional dimension of the blade members.

Referring now to FIGS. 14-14C, there is illustrated yet another embodiment of a surgical obturator in accordance with the present disclosure. Obturator 500 includes two components, namely, base member 520 defining a longitudinal axis "X" and an atraumatic tip member 530. Tip member 530 defines a generally tapered configuration and extends along longitudinal axis "X" from base member 520 to a penetrating end 515. Penetrating end 515 is defined at a point generally coinciding with the longitudinal axis "X" of the base portion 520. Tip member 530 may include a pair of diametrically opposed wing members 540a, 540b extending radially outward from an outer wall 535 of the tip member 530 and extending along the longitudinal axis "X" from base member 520 to a location proximal of penetrating end 515. As illustrated in detail in FIG. 14B, wings 540a, 540b define a cross-sectional dimension which increases from distal to proximal. In the alternative, as depicted in FIGS. 15-15C, a pair of diametrically opposed wings or blade members 550a, 550b with outward cutting edges extends radially outward from outer wall 535 of tip member 530 and along longitudinal axis "X" from base member 520 to penetrating end 515, as shown in FIG. 15. As illustrated in detail in FIG. 15A, blades 550a, 550b define a cross-sectional dimension which increases from distal to proximal. In this embodiment, blades 550a, 550b extend to and may include penetrating tip 515 and converge to define an arcuate configuration of penetrating end 515, as shown in FIG. 15B. This rounded blade tip arrangement may provide an advantageous configuration for tissue piercing/penetration.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical obturator for use in penetrating tissue, which comprises:
   an elongate obturator member defining a longitudinal obturator axis, and proximal and distal ends;
   an obturator tip connected to the obturator member, the obturator tip including from distal to proximal:
   a penetrating end;
   a substantially planar surface extending from the penetrating end and contiguous therewith; and
   a series of intersecting surfaces superposed on the planar surface and being symmetrically arranged about the longitudinal axis, the series of intersecting surfaces including from distal to proximal:
     a centrally disposed surface in general alignment with the longitudinal axis and contiguous with the planar surface;
     first side surfaces obliquely arranged on respective opposed sides of the centrally disposed surface in intersecting relation therewith; and
     second side surfaces obliquely arranged on respective opposed sides of the first side surfaces in intersecting relation therewith,
   wherein at least one of the series of intersecting surfaces is generally concave and wherein each of the first, second, and centrally disposed surfaces define an arcuate proximal edge.

2. The surgical obturator according to claim 1 wherein the obturator tip further includes:
   a second planar surface in opposed relation with the first-mentioned planar surface and in general parallel relation therewith; and
   a second series of intersecting surfaces extending from the second planar surface and being symmetrically arranged about the longitudinal axis, the second series of intersecting surfaces including:
     a centrally disposed surface in general alignment with the longitudinal axis and contiguous with the planar surface;
     first side surfaces on respective opposed sides of the centrally disposed surface in intersecting relation therewith; and
     second side surfaces on respective opposed sides of the first side surfaces in intersecting relation therewith.

3. The surgical obturator according to claim 2 wherein each of the surfaces of the series of surfaces is generally arcuate.

4. The surgical obturator according to claim 3 wherein each of the surfaces of the series of surfaces is generally concave.

5. The surgical obturator according to claim 2 wherein at least one of the surfaces of the series of surfaces is generally planar.

6. The surgical obturator according to claim 5 wherein each of the surfaces of the series of surfaces is generally planar.

7. The obturator according to claim 2 wherein the obturator tip is releasably mountable to the obturator member.

8. A surgical obturator for use in penetrating tissue, which comprises:
   an elongate obturator member;
   an obturator tip coupled with the obturator member, the obturator tip including a substantially planar member extending distally therefrom, the substantially planar member defining a pair of opposed planar surfaces and a distal penetrating end;
   first and second series of intersecting surfaces superposed on respective opposed planar surfaces of the substantially planar member, each of the first and second series of intersecting surfaces including, from proximal to distal:
     a centrally disposed surface extending in parallel relation to the respective planar surface;
     a pair of first side surfaces extending distally from an oblique intersection on opposed sides of the centrally disposed surface; and
     a pair of second side surfaces extending distally from an oblique intersection on opposed sides of the first side surfaces, wherein each of the first, second, and centrally disposed surfaces define an arcuate proximal edge and each of the respective arcuate proximal edges have a similar radius of curvature.

9. The surgical obturator according to claim 8, wherein the first and second series of intersecting surfaces are spaced laterally apart by the substantially planar member.

10. The surgical obturator according to claim 8, wherein the substantially planar member extends laterally outward from each of the second side surfaces.

11. The surgical obturator according to claim 8, wherein the first and second series of intersecting surfaces are symmetric about an axis defined by the substantially planar member.

* * * * *